US011034713B2

(12) United States Patent
Shunmugavel et al.

(10) Patent No.: US 11,034,713 B2
(45) Date of Patent: Jun. 15, 2021

(54) CRYSTALLINE MICROPOROUS MATERIAL MEDIATED CONVERSION OF C1-3 OXYGENATE COMPOUNDS TO C4 OXYGENATE COMPOUNDS

(71) Applicant: Haldor Topsøe A/S, Kgs. Lyngby (DK)

(72) Inventors: Saravanamurugan Shunmugavel, Lyngby (DK); Irantzu Sadaba Zubiri, Frederiksberg (DK); Esben Taarning, Frederiksberg (DK); Martin Spangsberg Holm, Oxford (GB)

(73) Assignee: Haldor Topsoe A/S, Lyngby (DK)

( * ) Notice: Subject to any disclaimer, the term of this patent is extended or adjusted under 35 U.S.C. 154(b) by 132 days.

(21) Appl. No.: 15/319,332

(22) PCT Filed: Jun. 18, 2015

(86) PCT No.: PCT/EP2015/063774
§ 371 (c)(1),
(2) Date: Dec. 15, 2016

(87) PCT Pub. No.: WO2015/193461
PCT Pub. Date: Dec. 23, 2015

(65) Prior Publication Data
US 2017/0129913 A1   May 11, 2017

(30) Foreign Application Priority Data
Jun. 19, 2014   (EP) .................................... 14173148

(51) Int. Cl.
| | | |
|---|---|---|
| *B01J 29/04* | (2006.01) | |
| *B01J 29/40* | (2006.01) | |
| *B01J 29/70* | (2006.01) | |
| *B01J 29/89* | (2006.01) | |
| *C01B 37/00* | (2006.01) | |
| *C01B 39/02* | (2006.01) | |
| *C01B 39/08* | (2006.01) | |
| *C01B 39/40* | (2006.01) | |
| *C01B 39/46* | (2006.01) | |
| *C07C 67/08* | (2006.01) | |
| *C07H 1/00* | (2006.01) | |
| *C07H 3/02* | (2006.01) | |
| *A23L 27/30* | (2016.01) | |
| *A23L 33/10* | (2016.01) | |
| *B01J 37/00* | (2006.01) | |
| *B01J 37/02* | (2006.01) | |
| *B01J 37/04* | (2006.01) | |
| *B01J 37/10* | (2006.01) | |
| *C07C 51/16* | (2006.01) | |
| *C07D 307/36* | (2006.01) | |

(52) U.S. Cl.
CPC ................ *C07H 1/00* (2013.01); *A23L 27/34* (2016.08); *A23L 33/10* (2016.08); *B01J 29/041* (2013.01); *B01J 29/405* (2013.01); *B01J 29/7049* (2013.01); *B01J 29/7057* (2013.01); *B01J 29/89* (2013.01); *B01J 37/0018* (2013.01); *B01J 37/0201* (2013.01); *B01J 37/04* (2013.01); *B01J 37/10* (2013.01); *C01B 37/005* (2013.01); *C01B 39/026* (2013.01); *C01B 39/085* (2013.01); *C01B 39/40* (2013.01); *C01B 39/46* (2013.01); *C07C 51/16* (2013.01); *C07C 67/08* (2013.01); *C07D 307/36* (2013.01); *C07H 3/02* (2013.01); *A23V 2002/00* (2013.01); *B01J 2229/186* (2013.01); *B01J 2229/37* (2013.01)

(58) Field of Classification Search
CPC .... B01J 29/405; B01J 29/7049; B01J 29/041; B01J 29/89
See application file for complete search history.

(56) References Cited

U.S. PATENT DOCUMENTS

| | | | |
|---|---|---|---|
| 6,300,494 B1 * | 10/2001 | Fleche | ...................... C07H 3/02 536/124 |
| 8,227,006 B2 | 7/2012 | Lee et al. | |
| 2009/0053781 A1 | 2/2009 | Hagiya et al. | |

FOREIGN PATENT DOCUMENTS

| | | |
|---|---|---|
| CN | 1810753 | 8/2006 |
| CN | 101024195 | 8/2007 |
| RU | 2 334 437 C2 | 9/2008 |
| WO | WO 97/43242 A1 | 11/1997 |
| WO | WO 03/042200 A1 | 5/2003 |

OTHER PUBLICATIONS

Dusselier, M. et al., ACS Catal., "Toward Functional Polyester Building Blocks from Renewable Glycolaldehyde with Sn Cascade Catalysis", 2013, vol. 3, pp. 1786-1800 (Year: 2013).*
SciFinder retrieval of 258 substances of molecular formula C4H8O4; obtained Sep. 26, 2018 (Year: 2018).*
Ungureanu, A. et al., Microporous and Mesoporous Materials, "Aldol condensation of aldehydes over semicrystalline zeolitic-mesoporous UL-ZSM-5", 2005, vol. 84, pp. 283-296 (Year: 2005).*
Guo, Q. et al., ChemSusChem Communications, "Highly Active and Recyclable Sn-MWW Zeolite Catalyst for Sugar Conversion to Methyl Lactate and Lactic Acid", 2013, vol. 6, pp. 1352-1356 (Year: 2013).*
Lew, C. et al., Microporous and Mesoporous Materials, "Tin-containing zeolite for the isomerization of cellulosic sugars", 2012, vol. 153, pp. 55-58 (Year: 2012).*

(Continued)

*Primary Examiner* — Bahar Craigo
(74) *Attorney, Agent, or Firm* — Blank Rome LLP

(57) ABSTRACT

A process for the preparation of $C_4$ oxygenate compounds such as threose, erythrose or erythrulose starting from a composition comprising $C_{1-3}$ oxygenate compounds such as formaldehyde, glycolaldehyde, glyoxal, pyruvaldehyde or acetol, wherein the process is carried out in the presence of a crystalline microporous material having a ring pore structure selected from an eight-membered ring pore structure or a ten-membered ring pore structure.

12 Claims, 2 Drawing Sheets

(56) References Cited

OTHER PUBLICATIONS

Figure 1:
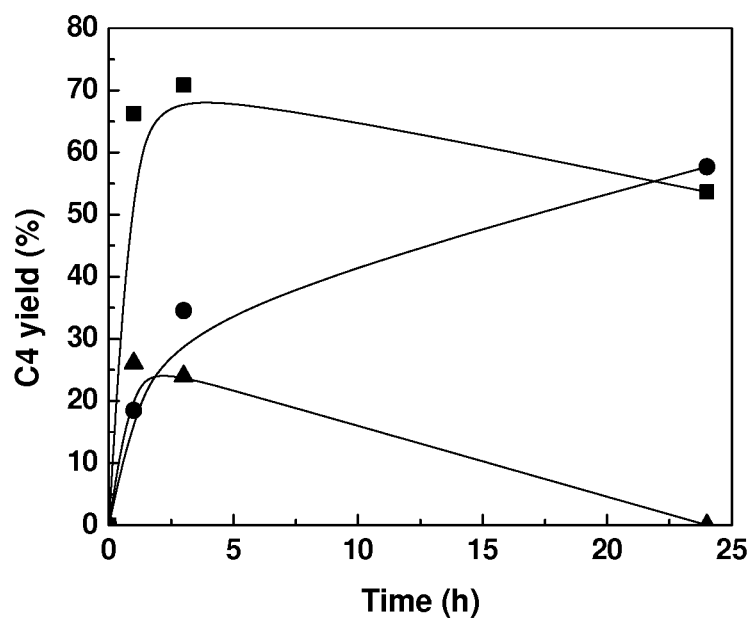

F. Seel, et al., Formattion of sugars and sugar-like products by UV irradiation of formaldehyde absorbed on zeolites. Zeitschrift fuer Naturforschung, Teil B: Anorganische Chemie, Organische Chemie, Jan. 11, 1981, vol. 36B, No. 11, pp. 1451-1456.

C. Cobzarus, et al., Gas phase aldol condensation of lower aldehydes over clinoptilolite rich natural zeolites. Applied Catalysis A: General, Oct. 5, 2008, vol. 351, No. 2, pp. 253-258, Section 2.1, Table 1, p. 253.

G T Kokotailo, et al., The framework topology of ZSM-22: A high silica zeolite. Zeolites, Nov. 31, 1985, vol. 5, No. 6, pp. 349-351.

M.S. Holm et al., "Sn-Beta Catalysed Conversion of Hemicellulosic Sugars." Green Chemistry, vol. 14, pp. 702-706, 2012.

E. Dumitriu et al., "The Aldol Condensation of Lower Aldehydes Over MFI Zeolites with Different Acidic Properties." Microporous and Mesoporous Materials, vol. 43, pp. 341-359, 2001.

I.V. Delidovich et al., "Catalytic Condensation of Glycolaldehyde and Glyceraldehyde with Formaldehyde in Neutral and Weakly Alkaline Aqueous Media: Kinetics and Mechanism." Kinetics and Catalysis, vol. 50, No. 2, pp. 297-303, 2009.

J. Li et al., "Hydrocarbon Oxidation and Aldol Condensation Over Basic Zeolite Catalysts." Catalysis Today, vol. 116, pp. 226-233, 2006.

I.V. Delidovich et al., "Nickel Phosphate Molecular Sieves VSB-5 as Heterogeneous Catalysts for Synthesis of Monosaccharides from Formaldehyde and Dihydroxyacetone." New J. Chem., vol. 36, pp. 2201-2204, 2012.

A. Corma, "Inorganic Solid Acids and Their Use in Acid-Catalyzed Hydrocarbon Reactions." Chem. Reviews, vol. 95, No. 3, 559-614, 1995.

\* cited by examiner

CRYSTALLINE MICROPOROUS MATERIAL MEDIATED CONVERSION OF C1-3 OXYGENATE COMPOUNDS TO C4 OXYGENATE COMPOUNDS

BACKGROUND

The selective and high yielding preparation of $C_4$ oxygenate compounds, e.g. $C_4$ sugars such as erythrose, threose and erythrulose, could prove valuable for their use in the chemical industry for the preparation of, for example: $C_4$ polyols; methyl vinyl glycolate or products obtainable therefrom; 2-hydroxy-4-methoxybutanoic acid or salts or esters thereof such as methyl 2-hydroxy-4-methoxybutanoate.

Known methods for preparing $C_4$ oxygenate compounds include the aldol self-condensation of glycolaldehyde. It has been observed that aldol condensations are not selective for the preparation of $C_4$ oxygenate compounds; a mix of products is observed as the $C_4$ product continues to react to form oxygenate compounds with a greater number of carbon atoms. In order to control the reaction's selectivity for $C_4$ oxygenate compounds, the formation of $C_4$-oxygenate and silicate or borate complexes, or the use of $C_4$-oxygenate selective catalysts is required.

An example of the use of a silicate complex for the selective formation of $C_4$ oxygenate compounds includes the aldol condensation of glycolaldehyde in the presence of aqueous sodium silicate; Science (2010) 327, pp 984-986. During the reaction a silicate-$C_4$-sugar complex is formed, consequently controlling the selectivity of the reaction. A further example includes the condensation of glycolaldehyde in the presence of a borate buffer. A high yield of $C_4$ oxygenate compounds ($C_4$ sugars) is obtained (86%); J. Am. Chem. Soc. (2011) 133, pp 9457-9468.

An example of a $C_4$-oxygenate selective catalyst includes the preparation of $C_4$ oxygenate compounds by the aldol condensation of glycolaldehyde in the presence of a homochiral dipeptide catalyst. The yield of $C_4$ oxygenate compound products was up to 63%; PNAS (2006) 103, pp 12712-12717. Alternatively, a zinc-proline catalyst may be used. The total yield of the $C_4$-sugar products was approximately 51%. $C_6$-sugars were formed in a yield of approximately 30%; Org. Biomol. Chem. (2005), 3, pp 1850-1855.

Alternative preparations of $C_4$ oxygenate compounds from glycolaldehyde include the proposed tetrose transient intermediate in the preparation of 2-hydroxy-4-methoxybutanoate ($C_4$) and methyl vinyl glycolate ($C_4$). The reaction proceeds in the presence of a zeotype catalyst. The zeotype material was Sn-BEA, a twelve-membered ring pore structure; Green Chemistry (2012), 14, pp 702-706.

An alternative zeotype material, such as a ten-membered ring pore structured zeotype (e.g. Sn-MFI or Ti-MFI), may be used to isomerise $C_2$ oxygenate compounds. Such a zeotype has been used for the isomerisation of glyoxal to glycolic acid. The yield of glycolic acid was approximately 90%; Green Chemistry (2014), 16, pp 1176-1186.

It is an object of the present invention to provide a process for the preparation of $C_4$ oxygenate compounds from a composition comprising $C_{1-3}$ oxygenate compounds, wherein the process is selective for the production of $C_4$ oxygenate compounds and the product is obtained in high yields.

DISCLOSURE OF THE INVENTION

It has now been discovered that glycolaldehyde may be selectively transformed into $C_4$ oxygenate compounds in the presence of a crystalline microporous material comprising a small- or medium-pore structure. The reaction proceeds in a high yield. Additionally, it is possible for the reaction to proceed in the presence of additional compounds to selectively form the desired $C_4$ oxygenate compounds.

The invention is further defined by a process for the preparation of $C_4$ oxygenate compounds from a composition comprising $C_{1-3}$ oxygenate compounds, wherein the process is carried out in the presence of a crystalline microporous material comprising a small- or medium-pore structure.

$C_4$ oxygenate compounds may be known as $C_4$ sugars or oxygenated compounds with a carbon chain length of four carbon atoms. The molecular formula of the $C_4$ oxygenate compounds may be $C_4H_8O_4$. $C_4$ oxygenate compounds may also be described as tetroses. The $C_4$ oxygenate compounds are selected from one or more of the group consisting of threose, erythrose and erythrulose.

In one embodiment of the invention compositions comprising $C_{1-3}$ oxygenate compounds comprise one or more oxygenate compounds selected from the group consisting of $C_1$ oxygenate compounds, $C_2$ oxygenate compounds and $C_3$ oxygenate compounds. $C_1$, $C_2$ and $C_3$ oxygenate compounds means compounds that have a carbon chain length of one, two or three carbon atoms respectively. The molecular formulae of the $C_{1-3}$ oxygenate compounds are formulae selected from one or more of the group consisting of: $CH_2O$; $C_2H_4O_2$; $C_2H_2O_2$; $C_3H_6O_2$ and $C_3H_4O_2$. Preferably, the composition comprising $C_{1-3}$ oxygenate compounds is a composition comprising one or more compounds selected from the group consisting of formaldehyde, glyoxal, glycolaldehyde, pyruvaldehyde and acetol. In a second embodiment, preferably the composition comprising $C_{1-3}$ oxygenate compounds is a composition comprising one or more $C_2$ oxygenate compounds selected from the group consisting of glycolaldehyde (2-hydroxyacetaldehyde) and glyoxal. Glycolaldehyde is a compound with a carbon chain length of two carbon atoms, also known as a $C_2$ oxygenate compound or $C_2$ sugar.

The composition comprising $C_{1-3}$ oxygenate compounds may be in the form of a solution, wherein the solvent is selected from the group consisting of water, methanol and a water and methanol mixture. For example, the composition comprising $C_{1-3}$ oxygenate compounds may be an aqueous or methanolic solution of glycolaldehyde or an aqueous or methanolic solution of a composition comprising one or more compounds selected from the group consisting of formaldehyde, glyoxal, glycolaldehyde, pyruvaldehyde and acetol.

Compositions comprising $C_{1-3}$ oxygenate compounds are obtainable by pyrolysis of biomass or pyrolysis of one or more oxygenate compounds selected from the group consisting of $C_5$ oxygenate compounds, $C_6$ oxygenate compounds and sucrose. $C_5$ oxygenate compounds and $C_6$ oxygenate compounds means one or more compounds selected from the group consisting of glucose, fructose, xylose and isomers thereof. Exemplary pyrolysis reactions are provided in U.S. Pat. No. 7,094,932 B2 and PCT/EP2014/053587.

Crystalline microporous material includes zeolite materials and zeotype materials. Zeolite materials are crystalline alumino-silicates with a microporous crystalline structure, according to Corma et al., Chem. Rev. 1995, 95 pp 559-614. The aluminum atoms of the zeolite material may be partly or fully substituted by a metal (metal atoms) such as zirconium (Zr), titanium (Ti) and tin (Sn), these materials are known as zeotype materials.

Crystalline microporous material comprising a small-pore structure means a crystalline microporous material comprising an eight-membered ring pore structure; crystalline microporous material comprising a medium-pore structure means a crystalline microporous material comprising a ten-membered ring pore structure. Examples of crystalline microporous materials with a small- or medium-pore structure are provided in Chem. Rev. 1995, 95 pp 559-614 and include structures such as LTA, CHA, MFI (ZSM-5), MEL, MTT, MWW, TON, HEU, AEL, AFO, MWW and FER.

The crystalline microporous material with a structure of BEA comprises a large, twelve-membered ring pore structure (Chem. Rev. 1995, 95 pp 559-614), and is not considered a feature of the present invention.

Examples of zeotype materials with a medium pore size include structures such as Sn-MFI, Ti-MFI and Zr-MFI. An example of a zeotype material with a small pore size is Sn-LTA.

Crystalline microporous materials comprising a small- or medium-pore structure may be considered to behave as a catalyst.

The percentage yield of $C_4$ oxygenate compounds prepared by the process of the present invention is equal to or greater than 20%, equal to or greater than 24%, equal to or greater than 27%, equal to or greater than 30%, equal to or greater than 35%.

The content of metal (metal atoms) in the crystalline microporous material comprising a small- or medium-pore structure is present from 0.1 to 15 wt %, from 0.5 to 5.0 wt %, from 0.5 to 1.5 wt %.

The process may be carried out in a solvent; wherein the solvent may be selected from one or more of the group consisting of water, alcohol and a water and alcohol mixture (water and alcohol). Alcohol may be selected from one or more of the group consisting of methanol and ethanol.

The process may be carried out at a temperature of from 25 to 150° C., from 50 to 120° C., and from 70 to 100° C.

The $C_4$ oxygenate compounds produced by the present invention may be converted to $C_4$-polyols by hydrogenation. Such hydrogenation reactions may be performed in the presence of a supported metal catalyst, wherein the metal is for example copper, nickel, molybdenum, cobalt, iron, chromium, zinc, and the platinum group metals. In a preferred embodiment the metal catalyst is selected from the group consisting of palladium or ruthenium supported on carbon or Raney nickel. Exemplary hydrogenation reaction conditions are disclosed in U.S. Pat. No. 6,300,494 B1 and U.S. Pat. No. 4,487,980 B1. Examples of further suitable metal catalysts and reaction conditions for use in hydrogenation reactions are disclosed in Ullmann's Encyclopaedia of Industrial Chemistry: Hydrogenation and Dehydrogenation.

The $C_4$ oxygenate compounds produced by the process of the present invention may be converted to methyl vinyl glycolate and 2-hydroxy-4-methoxybutanoic acid or salts or esters thereof. Science (2010) 328, pp 602-605 and Green Chemistry (2012) 14, pp 702-706 disclose appropriate synthetic procedures. Additionally, α-hydroxy-γ-butyrolactone may be prepared from the $C_4$ oxygenate compounds under the same conditions or conditions as described in ACS Catal., 2013, 3 (8), pp 1786-1800

The methyl vinyl glycolate compound may further react to form α-hydroxy methinonine analogues; an example of this transformation is disclosed in WO 98/32735. α-hydroxy methinonine analogues include compounds selected from the group consisting of 2-hydroxy-4-($C_{1-5}$alkylthio)butanoic acid, salts and esters thereof.

$C_{1-5}$alkylthio means an alkyl thiol selected from the group consisting of methane thiol, ethane thiol, straight or branched chain propane thiol, straight or branched chain butane thiol and straight or branched chain pentane thiol.

$C_{1-8}$ alkyl esters means esters comprising the alkyl group selected from the group consisting of methyl, ethyl, propyl, butyl, isopropyl, isobutyl, pentyl, hexyl, heptyl, octyl and 2-ethylhexyl.

In one embodiment of the invention the methionine α-hydroxy analogues is 2-hydroxy-4-(methylthio)butanoic acid.

In a second embodiment of the invention the methionine α-hydroxy analogues is selected from the group consisting of 2-hydroxy-4-(methylthio)butanoic acid methyl ester, 2-hydroxy-4-(methylthio)butanoic acid ethyl ester, 2-hydroxy-4-(methylthio)butanoic acid propyl ester, 2-hydroxy-4-(methylthio)butanoic acid butyl ester, 2-hydroxy-4-(methylthio)butanoic acid isopropyl ester, 2-hydroxy-4-(methylthio)butanoic acid pentyl ester, 2-hydroxy-4-(methylthio)butanoic acid hexyl ester, 2-hydroxy-4-(methylthio)butanoic acid heptyl ester, 2-hydroxy-4-(methylthio)butanoic acid octyl ester and 2-hydroxy-4-(methylthio)butanoic acid 2-ethylhexyl ester.

The $C_4$ oxygenate compounds produced by the process of the present invention may be converted into butanediols as described in ChemSusChem (2012) 5, pp 1991-1999.

The process for preparing $C_4$ oxygenate compounds from $C_{1-3}$ oxygenate compounds may also be carried out concomitantly with the hydrogenation reaction of the $C_4$ oxygenate compounds to form $C_4$ polyols. The reactions therefore may be conducted in one step, i.e. a 'one pot' reaction. A 'one-step' or 'one-pot' reaction means that the crystalline microporous material for the conversion of glycolaldehyde to $C_4$ oxygenate compounds and the metal catalyst for the hydrogenation of the $C_4$ oxygenate compounds are present in the reaction vessel simultaneously. The reaction is quenched when the hydrogenated product ($C_4$ polyols) is present.

$C_4$ polyol means $C_4$ oxygenate compounds that comprise compounds of a chain length of four carbon atoms and each carbon atom is bonded to an alcohol (OH) functional group. $C_4$ polyols may also be known as four carbon sugar alcohols and have the molecular formula of $C_4H_{10}O_4$. $C_4$ polyols are compounds selected from one or more of the group consisting of erythritol and threitol. Erythritol and threitol include all stereoisomers such as D- and L-threitol. Erythritol may be used as a foodstuff, a sweetener and for the preparation of butanediols. ChemSusChem (2012) 5, pp 1991-1999 illustrates the preparation of butanediols from erythritol.

EXAMPLE 1

Crystalline Microporous Material (Sn-MFI, Ti-MFI, Sn-BEA and Sn-LTA) Preparation:

Sn-MFI:

200 Sn-MFI (Si/Sn=200) is prepared according to the method described by Mal et al. (Mal, N. K.; Ramaswamy, V.; Ra-jamohanan, P. R.; Ramaswamy, A. V. Sn-MFI molecular sieves: Synthesis methods, 29Si liquid and solid MAS-NMR, 119Sn static and MAS NMR studies. Microporous Mater., 1997, 12, 331-340). According to this procedure $NH_4F$ (5.35 g) is dissolved in demineralized water (25.0 g). A solution of $SnCl_4.5H_2O$ (0.25 g) in $H_2O$ (10.0 g) is added under rapid stirring. After this, of tetrapropylammonium bromide [TPABr (9.8 g)] in $H_2O$ (56.0 g) is added slowly. Fumed silica (8.6 g) is dissolved in the mixture. The mixture is stirred for 3 hours and the gel is then transferred to a Teflon lined autoclave and crystallized at 200° C. for 6 days. The product is then suction filtrated with ample water and dried over-night at 80° C. Recovered powder is calcined at 550° C. (2° C./min) for 6 hours. 400Sn-MFI (Si/Sn=400) is prepared following the same procedure but adjusting the amount of $SnCl_4.5H_2O$.

Sn-MFI (Alternative Preparation):

200 Sn-MFI (Si/Sn=200) can be prepared from ZSM-5 (Ze-ochem, ZEOcat® PZ-2 100H). ZSM-5 is treated under steam at 450° C. for 6 h, acid washed with HCl 1 M at 100° C. for 16 h, and washed with ample water. The solid is dried at 120° C. for 16 h, impregnated with an aqueous solution of $SnCl_2$ and calcined at 550° C. (2° C./min) for 6 h.

Ti-MFI:

200 Ti-MFI (Si/Ti=200) is prepared according to a modification of the method described by Mal et al. (Mal, N. K.; Ramaswamy, V.; Rajamohanan, P. R.; Ramaswamy, A. V. Sn-MFI molecular sieves: Synthesis methods, 29Si liquid and solid MAS-NMR, 119Sn static and MAS NMR studies. Microporous Mater., 1997, 12, 331-340). According to this procedure $NH_4F$ (5.35 g) is dissolved in demineralized water (25.0 g). A solution of Ti (IV) ethoxide (0.17 g) in $H_2O$ (3.5 g) and $H_2O_2$ (6.5 g) is added under rapid stirring. After this, a solution of tetrapropylammonium bromide [TPABr (9.8 g)] in $H_2O$ (56.0 g) is added slowly. Fumed silica (8.6 g) is dissolved in the mixture. The mixture is stirred for 20 hours and the gel is then transferred to a Teflon lined autoclave and crystallized at 200° C. for 6 days. The product is then suction filtrated with ample water and dried overnight at 80° C. Recovered powder is calcined at 550° C. (2° C./min) for 6 hours.

Sn-BEA:

Sn-BEA was prepared according to the method described in EP 2184270 B1.

Sn-LTA:

125 Sn-LTA with (Si/Sn=125) can be prepared from LTA zeolite (Sigma-Aldrich, Molecular sieves, 4Å). LTA is treated under steam at 450° C. for 6 h, acid washed with HCl 1 M at 100° C. for 16 h, and washed with ample water. The solid is dried at 120° C. for 16 h, impregnated with an aqueous solution of $SnCl_2$ and calcined at 550° C. (2° C./min) for 6 h.

Preparation of $C_4$ oxygenate compounds from glycolaldehyde:

EXAMPLE 2

Crystalline microporous material (0.15 g) prepared according to Example 1, glycolaldehyde dimer [SAFC, 0.25 g] and deionized water (5 g) are added in a 20 mL vial (Ace pressure tube) and heated at 80° C. under vigorous stirring (600 rpm). Samples of the reaction are taken at selected times (0.5-24 h). Analysis of the liquid samples after filtration is carried out using a HPLC Agilent 1200 equipped with a BIORAD Amminex HPX-87H column at 65° C. and 0.004 M $H_2SO_4$ solution in water at 0.6 ml $min^{-1}$.

TABLE 1

The percentage yield of $C_4$ oxygenate compounds produced from an aqueous glycolaldehyde solution over time with various crystalline microporous materials.

| | Percentage yield (%) of $C_4$-oxygenate compounds | | | | |
|---|---|---|---|---|---|
| Time (h) | 400Sn-MFI | 200Sn-MFI | Ti-MFI | Sn-BEA | Sn-LTA |
| 1 | 30.8 | 66.3 | 18.5 | 26.1 | 37.5 |
| 3 | 59.2 | 70.8 | 34.5 | 23.9 | 51.17 |
| 24 | 73.4 | 53.6 | 57.7 | 0 | 55.58 |

EXAMPLE 3

Compositions comprising $C_{1-3}$ oxygenate compounds may be prepared by pyrolysis of biomass or $C_{5-6}$ sugars ($C_{5-6}$ oxygenate compounds) such as glucose, sucrosqe, fructose or xylose. Exemplary pyrolysis reactions are provided in U.S. Pat. No. 7,094,932 B2 and PCT/EP2014/053587. The $C_{1-3}$ oxygenate compositions comprise 5 wt % glycolaldehyde or greater, such as between 5 wt % and 65 wt %.

A composition comprising $C_{1-3}$ oxygenate compounds obtained from the pyrolysis of glucose according to U.S. Pat. No. 7,094,932 B2 is diluted in water to obtain 5 g of a solution comprising 8 wt % glycolaldehyde. Crystalline microporous material (0.15 g), prepared according to Example 1 is added to the mixture in a 20 mL vial (Ace pressure tube) and the reaction is heated at 80° C. under vigorous stirring (600 rpm). Samples of reaction are taken at selected times (0.5-24 h). Analysis of the liquid samples after filtration is carried out as previously explained.

TABLE 2

The percentage yield of $C_4$ oxygenate compounds produced from an aqueous solution of a $C_{1-3}$ oxygenate mixture according to Example 2 versus time. Various crystalline microporous materials are shown.

| | Percentage yield (%) of $C_4$ oxygenate compounds | | | |
|---|---|---|---|---|
| Time (h) | 400Sn-MFI | 200Sn-MFI | Ti-MFI | Sn-BEA |
| 1 | 7.7 | 21.7 | 6.7 | 7.4 |
| 3 | 13.1 | 35.5 | 11.2 | 22.5 |
| 24 | 39.4 | 52.9 | 40.2 | 21.8 |

EXAMPLE 4

Hydrogenation of $C_4$ oxygenate compounds is carried out in an autoclave reactor at pressures 30-90 bar of $H_2$. The reaction is carried out by addition of a composition comprising $C_4$ oxygenate compounds (15 g), prepared according to Example 2 or 3, into a Parr autoclave (50 mL) together with of Ru/C catalyst (0.2 g; 5% on activated charcoal from Aldrich). The reactor is heated at 80° C. and stirred at 500 rpm for 3 h.

EXAMPLE 5

Concomitant conversion of glycolaldehyde to $C_4$ oxygenate compounds and subsequent hydrogenation. ('one-pot' or 'one-step' conversion and hydrogenation).

Glycolaldehyde dimer (SAFC, 0.25 g), Sn-MFI (0.1 g) prepared according to Example 1, Ru/C catalyst (0.075 g; 5% on activated charcoal from Aldrich) and water (15 g) are added in a 50 mL Parr autoclave. The first condensation reaction is carried out at 80° C. in air atmosphere. After 3 h of reaction, the autoclave is pressurized with hydrogen at 90 bar and the reaction is allowed to proceed for 3 h. Samples of the products are obtained after the condensation step and the hydrogenation and analyzed after filtration in an HPLC as previously explained.

Alternatively, vinyl glycolic acid or methyl vinyl glycolate (MVG) can be obtained by reaction of a composition comprising $C_4$ oxygenate compounds prepared according to Examples 1 or 2 with Sn-BEA catalyst in water or methanol respectively; Green Chemistry (2012) 14, pp 702-706.

FIG. 1: The percentage yield of $C_4$ oxygenate compounds prepared according to Example 2 versus time. Various crystalline microporous materials are shown. The crystalline microporous materials are:
Squares: 200Sn-MFI;
Circles: Ti-MFI;
Triangles: Sn-BEA.

Figure 2:
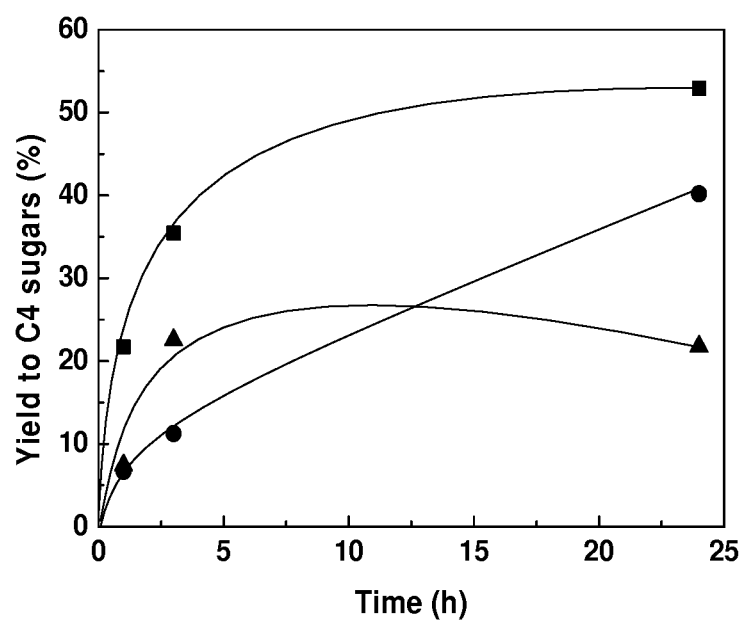

FIG. 2: The percentage yield of $C_4$ oxygenate compounds prepared according to Example 3 versus time. Various crystalline microporous materials are shown.
The crystalline microporous materials are:
Squares: 200Sn-MFI;
Circles: Ti-MFI;
Triangles: Sn-BEA.

The invention claimed is:

1. A process for the preparation of one or more $C_4$ oxygenate compounds of the formula $C_4H_8O_4$ from a composition comprising $C_{1-3}$ oxygenate compounds, the $C_4$ oxygenate compounds selected from one or more of the group consisting of threose, erythrose and erythrulose, wherein the composition comprising $C_{1-3}$ oxygenate compounds comprises glycolaldehyde and wherein the $C_4$ oxygenates are selectively formed from glycolaldehyde in the presence of a solvent and a crystalline microporous material comprising a zeotype material comprising a metal selected from one or more of the group consisting of zirconium, aluminum, tin or titanium and having a structure selected from the group consisting of CHA, LTA, MFI, MEL, MTT, MWW, TON, HEU, AEL, AFO, and FER, wherein the $C_4$ oxygenate compounds do not further react to form oxygenate compounds with a greater number of carbon atoms.

2. The process according to claim 1, wherein the composition comprising $C_{1-3}$ oxygenate compounds further comprises one or more compounds selected from the group consisting of formaldehyde, glyoxal, pyruvaldehyde and acetol.

3. The process according to claim 2, wherein the composition comprising $C_{1-3}$ oxygenate compounds comprises glycolaldehyde at a concentration of at least 5 wt %.

4. The process according to claim 1, wherein the solvent is selected from one or more of the groups consisting of water, alcohol and a water and alcohol mixture.

5. The process according to claim 4, wherein the alcohol is selected from one or more of the group consisting of methanol and ethanol.

6. The process according to claim 1, wherein the crystalline microporous material comprises from 0.1 wt % to 15 wt % of the metal.

7. The process according to claim 1, wherein the process is carried out at a temperature between 25° C. and 150° C.

8. The process according to claim 1, further comprising the step of hydrogenating the $C_4$ oxygenate compounds.

9. The process according to claim 1, wherein the process is a one-step process.

10. The process according to claim 1, further comprising the steps of isomerizing and esterifying the $C_4$ oxygenate compounds in the presence of Sn zeolite beta (Sn-BEA).

11. The process according to claim 1, further comprising the step of converting the $C_4$ oxygenate compounds to one or more compounds selected from the group consisting of erythritol and threitol.

12. The process according to claim 1, wherein a prior step is performed of pyrolyzing biomass or one or more oxygenate compounds selected from the group consisting of fructose, glucose, sucrose, xylose or isomers thereof, to produce a composition comprising the $C_{1-3}$ oxygenate compounds.

* * * * *